US012589064B2

(12) United States Patent
Chung et al.

(10) Patent No.: US 12,589,064 B2
(45) Date of Patent: Mar. 31, 2026

(54) TROLOX-PEPTIDE CONJUGATE AND USE THEREOF

(71) Applicant: Caregen Co., Ltd., Gyeonggi-do (KR)

(72) Inventors: Yong Ji Chung, Seoul (KR); Eun Mi Kim, Gyeonggi-do (KR); Eung Ji Lee, Gyeonggi-do (KR); Min Woong Kim, Incheon (KR)

(73) Assignee: Caregen Co., Ltd., Gyeonggi-do (KR)

( * ) Notice: Subject to any disclaimer, the term of this patent is extended or adjusted under 35 U.S.C. 154(b) by 1176 days.

(21) Appl. No.: 17/607,115

(22) PCT Filed: May 6, 2020

(86) PCT No.: PCT/KR2020/005967

§ 371 (c)(1),
(2) Date: Jul. 11, 2022

(87) PCT Pub. No.: WO2020/226419

PCT Pub. Date: Nov. 12, 2020

(65) Prior Publication Data

US 2023/0181441 A1 Jun. 15, 2023

(30) Foreign Application Priority Data

May 7, 2019 (KR) ........................ 10-2019-0053080

(51) Int. Cl.

| | |
|---|---|
| ***A61K 8/49*** | (2006.01) |
| ***A61K 8/64*** | (2006.01) |
| ***A61K 47/64*** | (2017.01) |
| ***A61P 17/14*** | (2006.01) |
| ***A61Q 7/00*** | (2006.01) |
| ***C07K 7/06*** | (2006.01) |
| ***C07K 7/08*** | (2006.01) |

(52) U.S. Cl.

CPC ................ *A61K 8/498* (2013.01); *A61K 8/64* (2013.01); *A61K 47/64* (2017.08); *A61P 17/14* (2018.01); *A61Q 7/00* (2013.01); *C07K 7/06* (2013.01); *C07K 7/08* (2013.01); *A61K 2800/57* (2013.01)

(58) Field of Classification Search

CPC .......... A61K 8/498; A61K 47/64; A61K 8/64; A61P 17/14; A61Q 7/00; C07K 7/06; C07K 7/08

See application file for complete search history.

(56) References Cited

U.S. PATENT DOCUMENTS

| | | | | |
|---|---|---|---|---|
| 5,272,252 A * | 12/1993 | McLean | A61P 11/16 530/324 |
| 6,974,794 B1 | 12/2005 | Adamson et al. | |
| 7,790,768 B2 | 9/2010 | Gan et al. | |
| 7,939,495 B2 * | 5/2011 | Chung | A61P 17/16 514/21.6 |
| 8,106,017 B2 * | 1/2012 | Chung | A61P 1/02 514/20.7 |
| 8,232,317 B2 | 7/2012 | Gan et al. | |
| 8,497,241 B2 | 7/2013 | Chung et al. | |
| 8,501,689 B2 | 8/2013 | Chung et al. | |
| 8,501,806 B2 | 8/2013 | Baroni et al. | |
| 8,729,028 B2 | 5/2014 | Chung et al. | |
| 9,913,817 B2 | 3/2018 | Baroni et al. | |
| 10,874,709 B2 * | 12/2020 | Chung | A61Q 5/00 |
| 11,357,783 B2 | 6/2022 | Chung et al. | |
| 11,617,796 B2 | 4/2023 | Chung et al. | |
| 2006/0210515 A1 | 9/2006 | Mower | |
| 2006/0210609 A1 | 9/2006 | Mower | |
| 2010/0047294 A1 | 2/2010 | Ahlnas | |
| 2010/0056619 A1 | 3/2010 | Thompson et al. | |
| 2010/0137238 A1 | 6/2010 | Gan et al. | |
| 2011/0160131 A1 | 6/2011 | Chung et al. | |
| 2011/0288058 A1 | 11/2011 | Baroni et al. | |
| 2011/0312884 A1 | 12/2011 | Chung et al. | |
| 2012/0245086 A1 | 9/2012 | Chung et al. | |
| 2019/0192677 A1 | 6/2019 | Chung et al. | |
| 2019/0374599 A1 * | 12/2019 | Chung | A61Q 5/02 |
| 2020/0289526 A1 | 9/2020 | Chung et al. | |
| 2024/0285780 A1 * | 8/2024 | Chung | A61P 17/00 |

FOREIGN PATENT DOCUMENTS

| | | |
|---|---|---|
| CN | 102027008 A | 4/2011 |
| CN | 102712685 A | 10/2012 |
| CN | 107428841 A | 12/2017 |
| CN | 109715217 A | 5/2019 |
| FR | 2 945 938 A1 | 12/2010 |
| JP | H04-506203 A1 | 10/1992 |
| JP | 2006-512285 A1 | 4/2006 |
| JP | 2006-519181 A | 8/2006 |

(Continued)

OTHER PUBLICATIONS

Ohn; EMBO Mol Med 2021, 13, e13790. https://doi.org/10.15252/emmm.202013790 (Year: 2021).*

Uno; J. Inv. Derm. 1993, 101, S143-S147. https://doi.org/10.1016/0022-202X(93)90516-K (Year: 1993).*

Alopecia from Merck Manual, pp. 1-9. Accessed Nov. 2, 2020. (Year: 2020).*

Alopecia Areata from Merck Manual, pp. 1-3. Accessed Nov. 2, 2020. (Year: 2020).*

PCT International Search Report and Written Opinion for PCT Application No. PCT/KR2020/005967 mailed Dec. 2, 2020 (8 pages).

(Continued)

*Primary Examiner* — Daniel R Carcanague

(74) *Attorney, Agent, or Firm* — Merchant & Gould P.C.

(57) ABSTRACT

The present invention relates to a Trolox-peptide conjugate having a structure in which Trolox and a peptide are chemically bonded. The Trolox-peptide conjugate not only very effectively inhibits the activity of 5α-reductase, but also inhibits the death of papilla cells and keratinocytes, promotes the growth thereof, and has antioxidative effects, and thus can remarkably promote hair formation while avoiding or preventing hair loss.

9 Claims, 14 Drawing Sheets

Specification includes a Sequence Listing.

(56) References Cited

FOREIGN PATENT DOCUMENTS

| | | | |
|---|---|---|---|
| JP | 2011-519358 | A | 7/2011 |
| JP | 2012-510963 | A | 5/2012 |
| JP | 2012-515769 | A | 7/2012 |
| JP | 2013-503856 | A | 2/2013 |
| KR | 960704555 | A | 10/1996 |
| KR | 20030087446 | A | 11/2003 |
| KR | 10-2010-0092150 | A | 8/2010 |
| KR | 20160023224 | A | 3/2016 |
| KR | 20180020789 | A | 2/2018 |
| KR | 10-2018-0112003 | A | 10/2018 |
| WO | 2008/020112 | A1 | 2/2008 |
| WO | 2017/159922 | A1 | 9/2017 |
| WO | 2018/034453 | A1 | 2/2018 |

OTHER PUBLICATIONS

Arai et al., "Design, Synthesis, and Evaluation of Trolox-Conjugated Amyloid-Beta C-Terminal Peptides for Therapeutic Intervention in an in vitro Model of Alzheimer's Disease," Bioorganic & Medicinal Chemistry, 2016, 24:4138-4143.

Notice of Allowance issued on Aug. 7, 2023 for the corresponding Chinese patent application No. 202080033954.6 (4 pages).

Extended European Search Report for European Patent Application No. 20802679.9 mailed Jul. 22, 2022, 7 pages.

Japanese Office Action for Japanese Patent Application No. 2021-565859 mailed Oct. 4, 2022, 4 pages.

Chinese Office Action for corresponding Patent Application No. 202080033954.6 issued on Feb. 22, 2023 (18 pages).

Final Rejection issued on May 30, 2023 for the corresponding Japanese patent application Appl. No. 2021-565859 (5 pages).

Miki Akamatsu and Toshio Fujita, "Quantitative Analysis and Prediction of Hydrophobicity of Oligopeptides", Organic Synthetic Chemistry, 1991, vol. 49, No. 9, pp. 836-845.

Jun Nozue and Yasuyuki Shigatani., "Color Materials", vol. 65, No. 5, 1992, pp. 317-325.

Rodrigo A. Quintanilla, et al., "Trolox and 17 β—Estradiol Protect against Amyloid β—Peptide Neurotoxicity by a Mechanism That Involves Modulation of the Wnt Signaling Pathway", The Journal of Biological Chemistry, 2005, vol. 280, No. 12, pp. 11615-11625.

Stephane Terry, et al., "Multifaceted Interaction Between the Androgen and Wnt Signaling Pathways and the Implication for Prostate Cancer", Journal of Cellular Biochemistry, 2006,vol. 99, pp. 402-410.

* cited by examiner

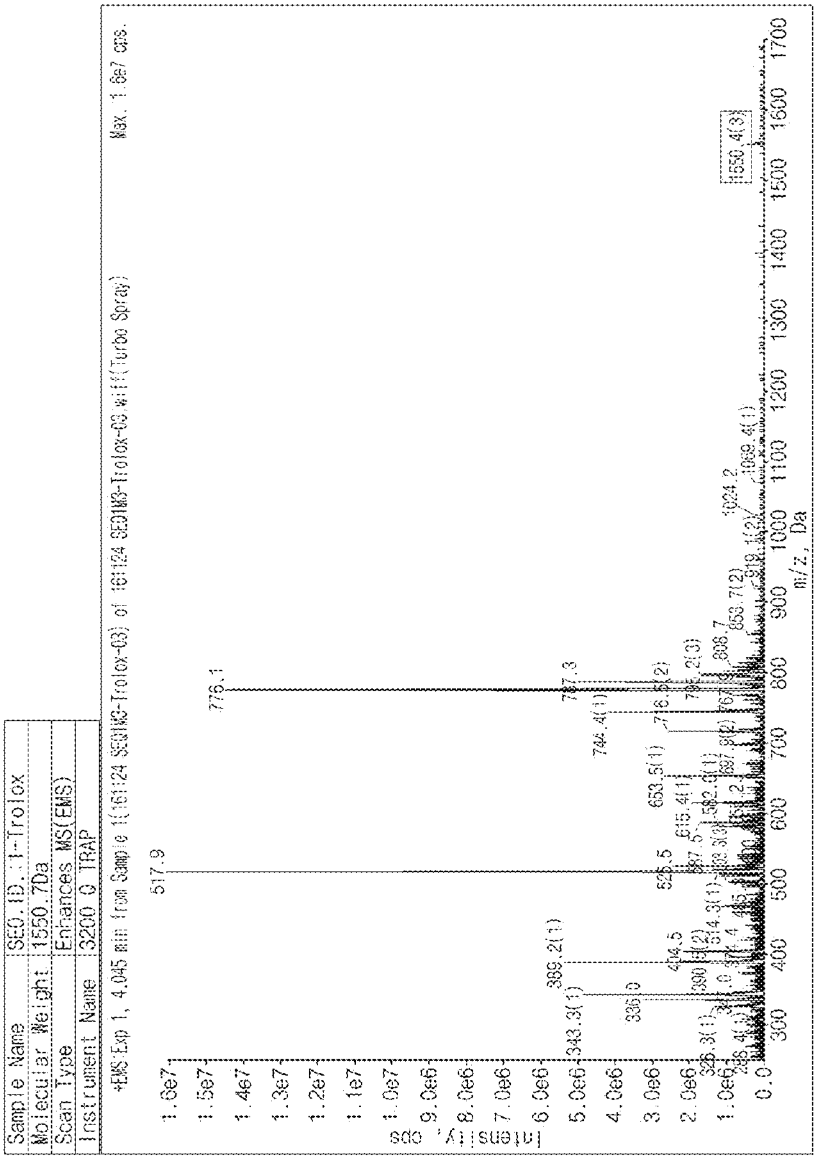
[Figure 1]

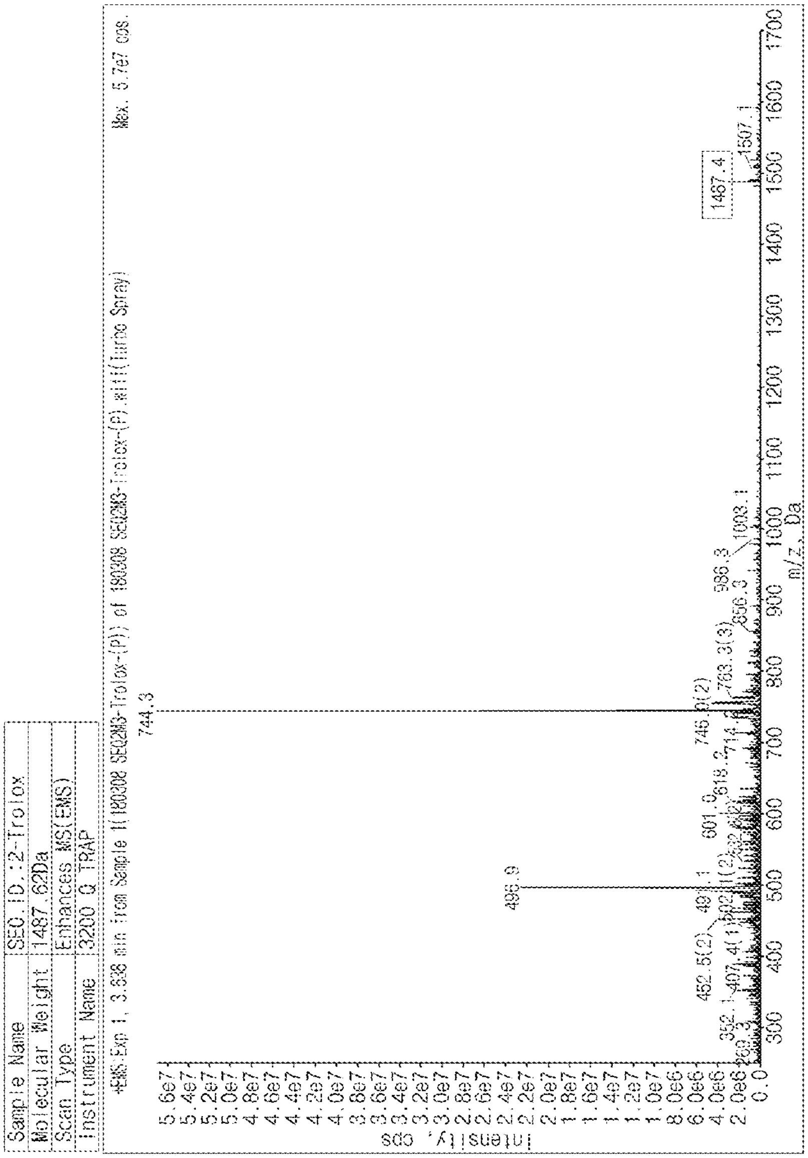
[Figure 2]

[Figure 3]
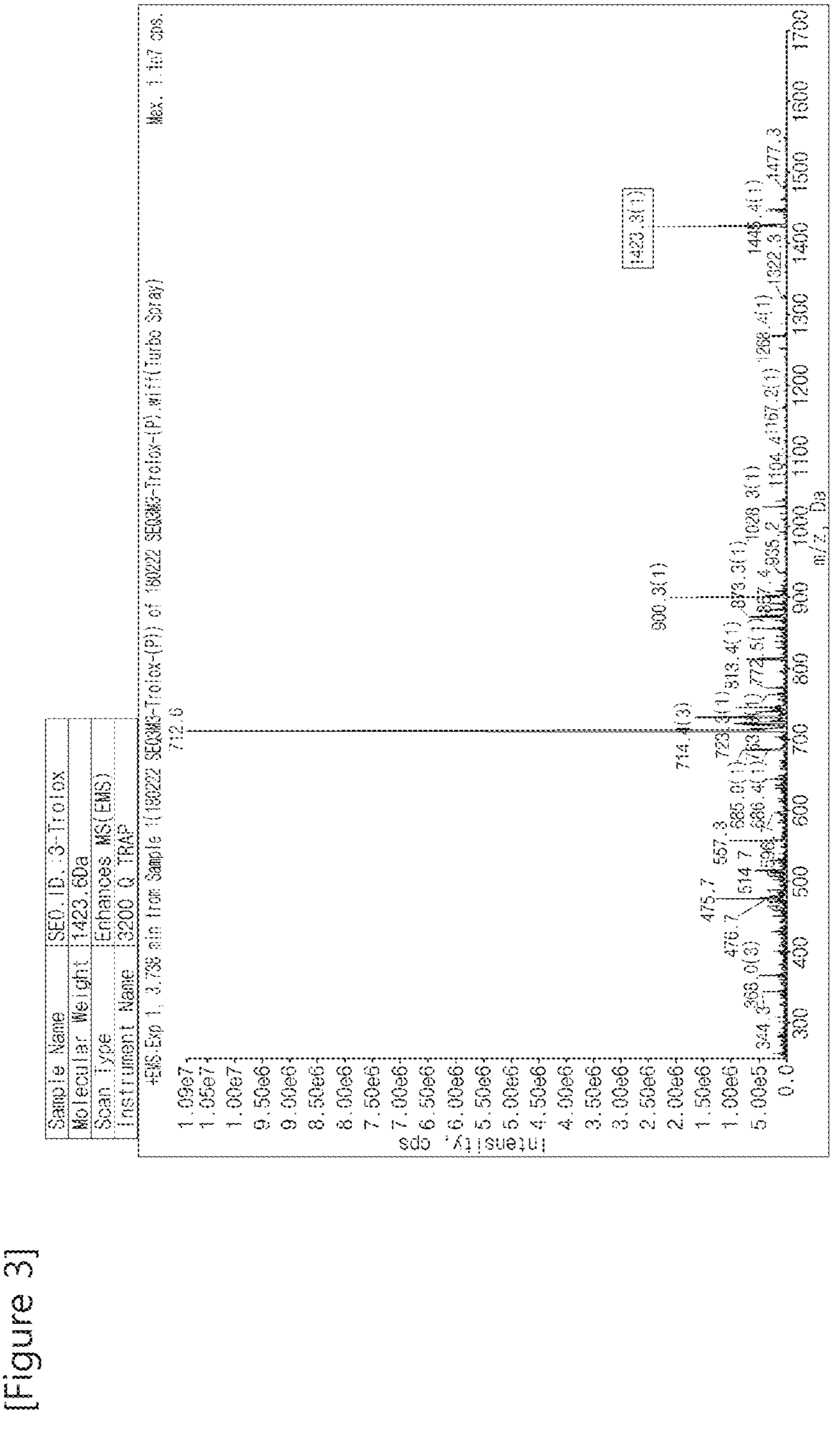

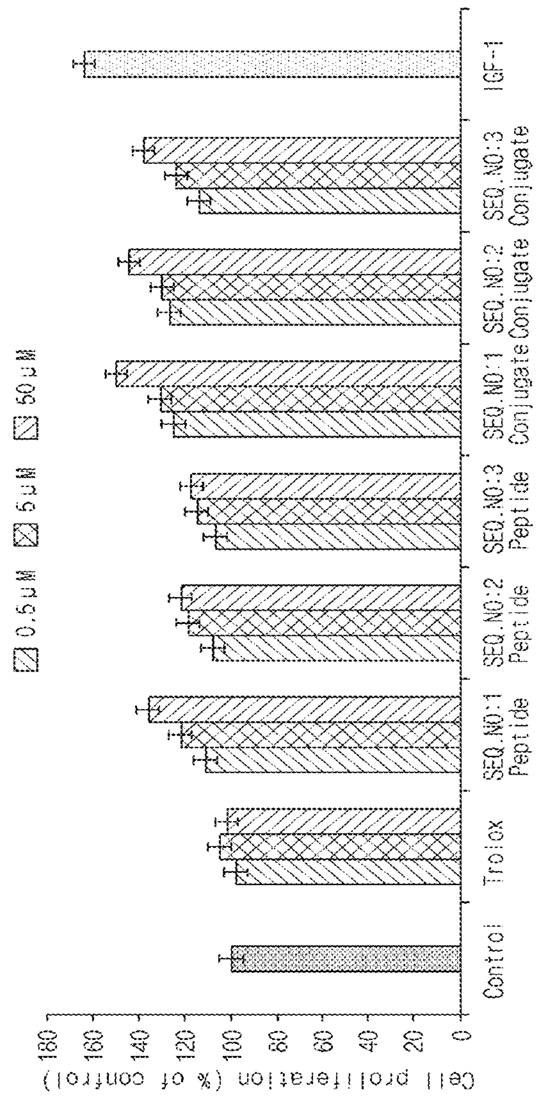
[Figure 4]

[Figure 5]
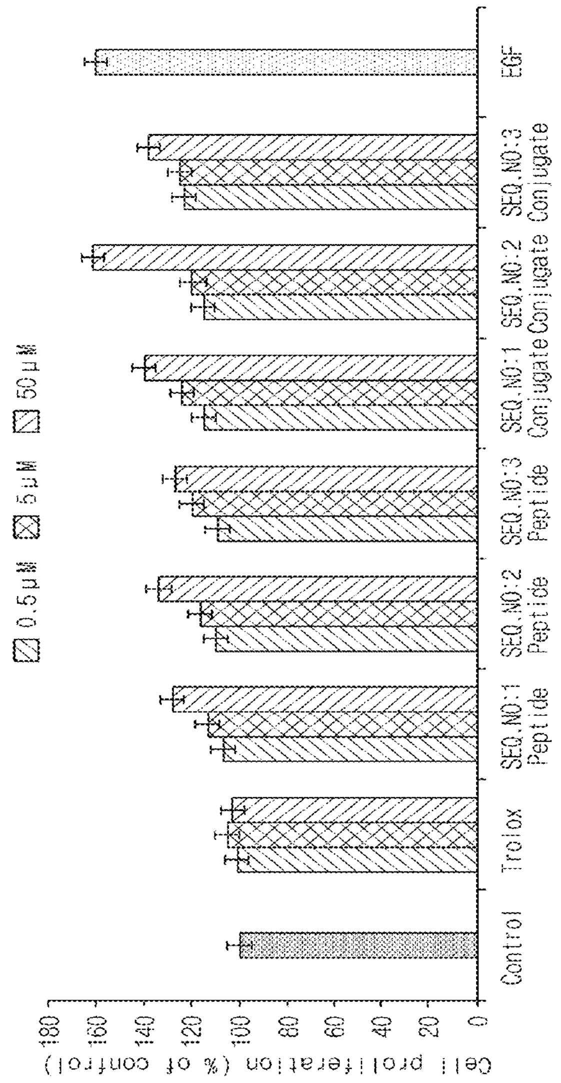

【Figure 6】
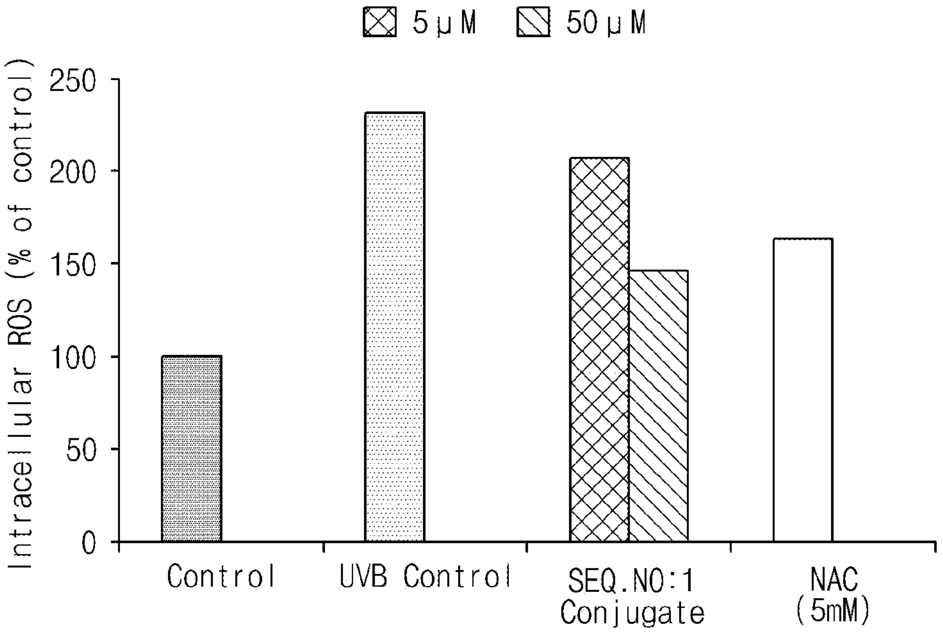
【Figure 7】
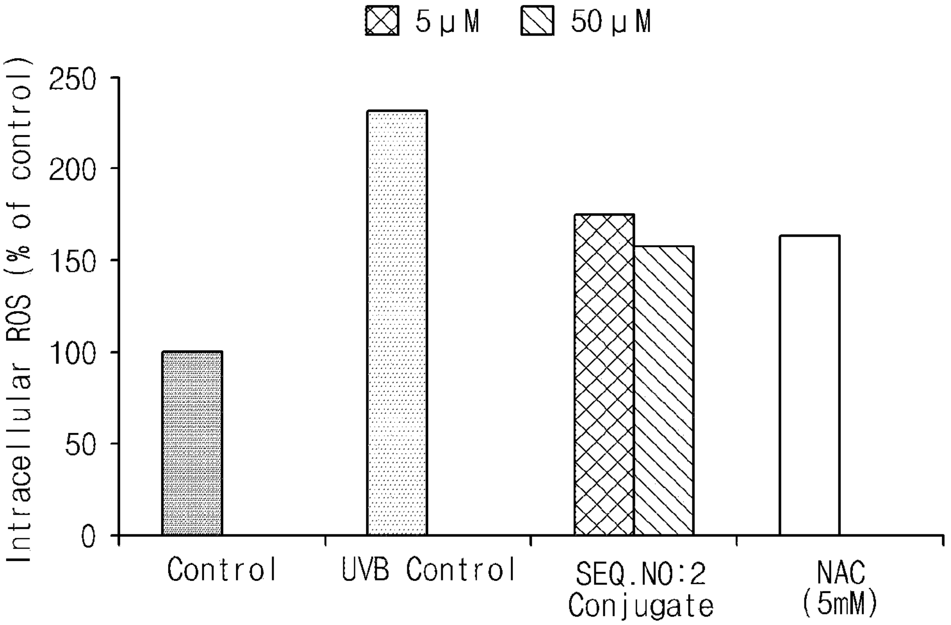

【Figure 8】
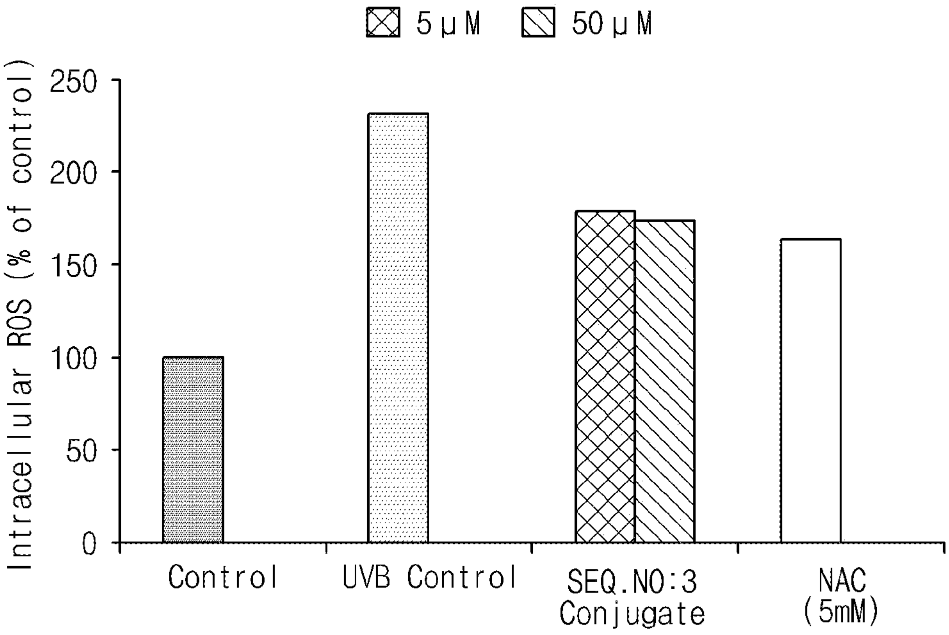

【Figure 9】
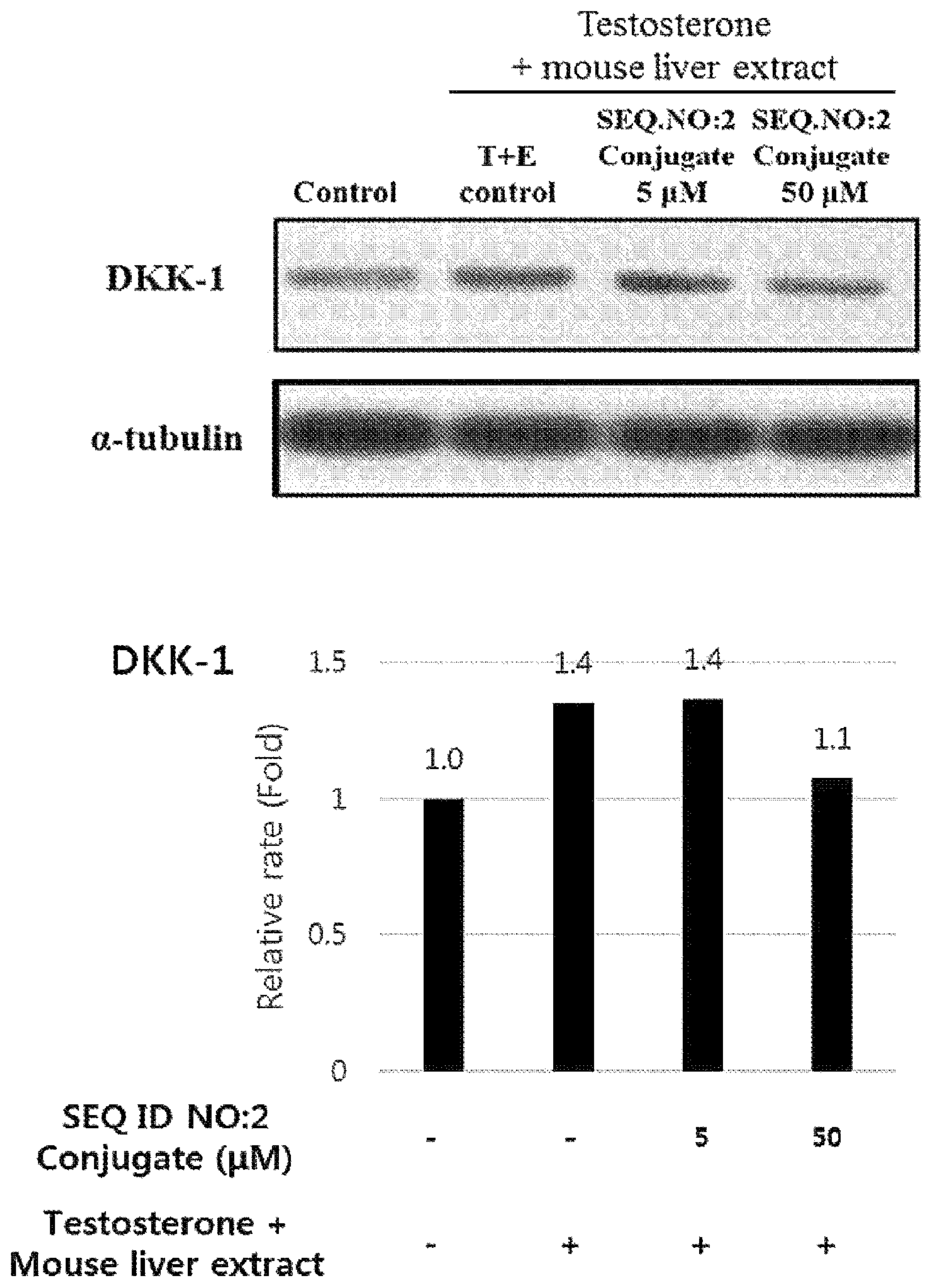

【Figure 10】
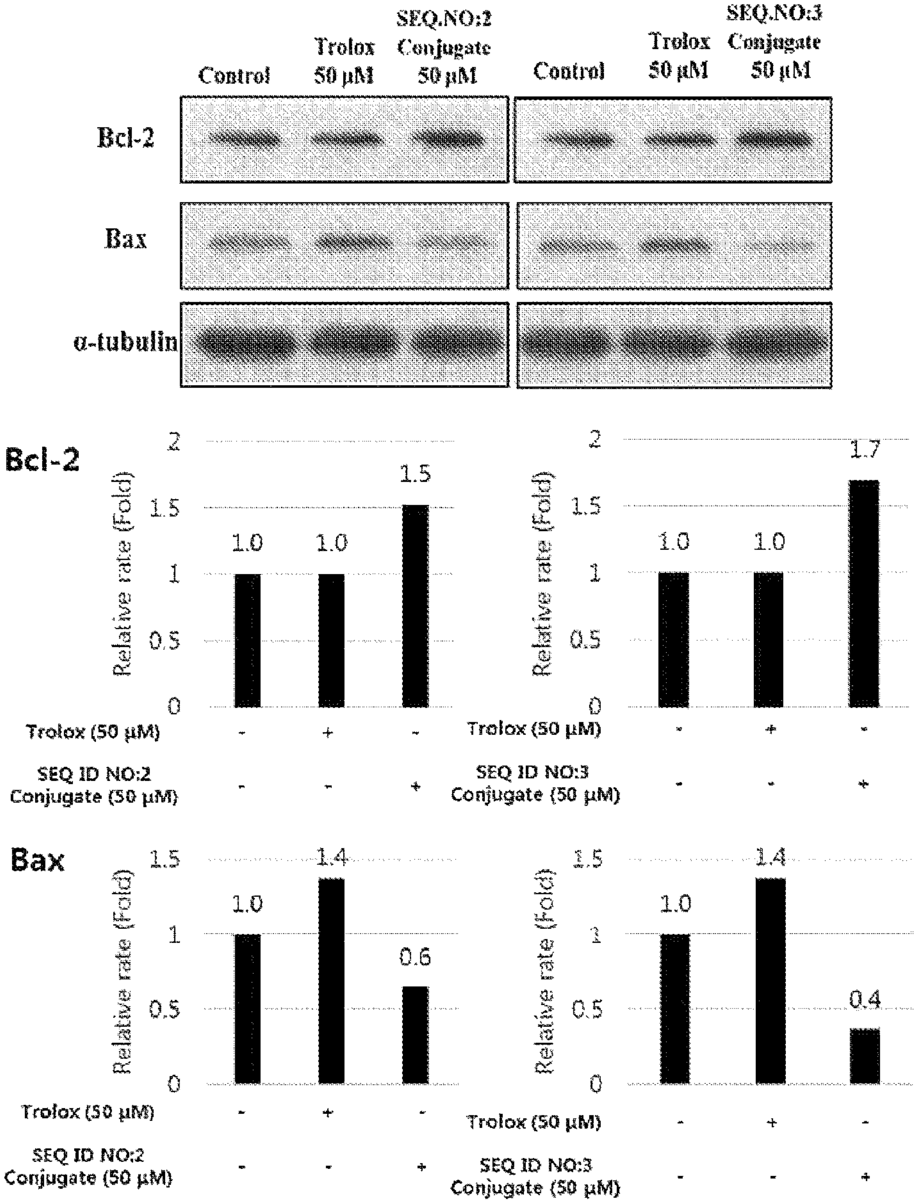

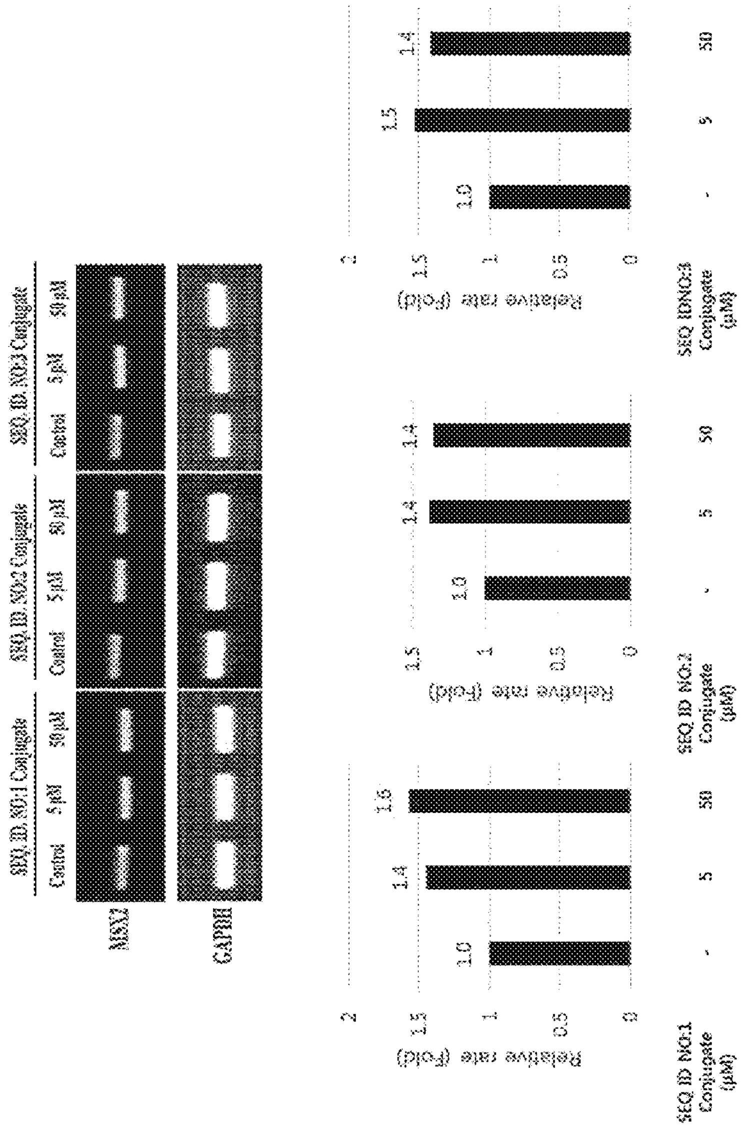
[Figure 11]

[Figure 12]
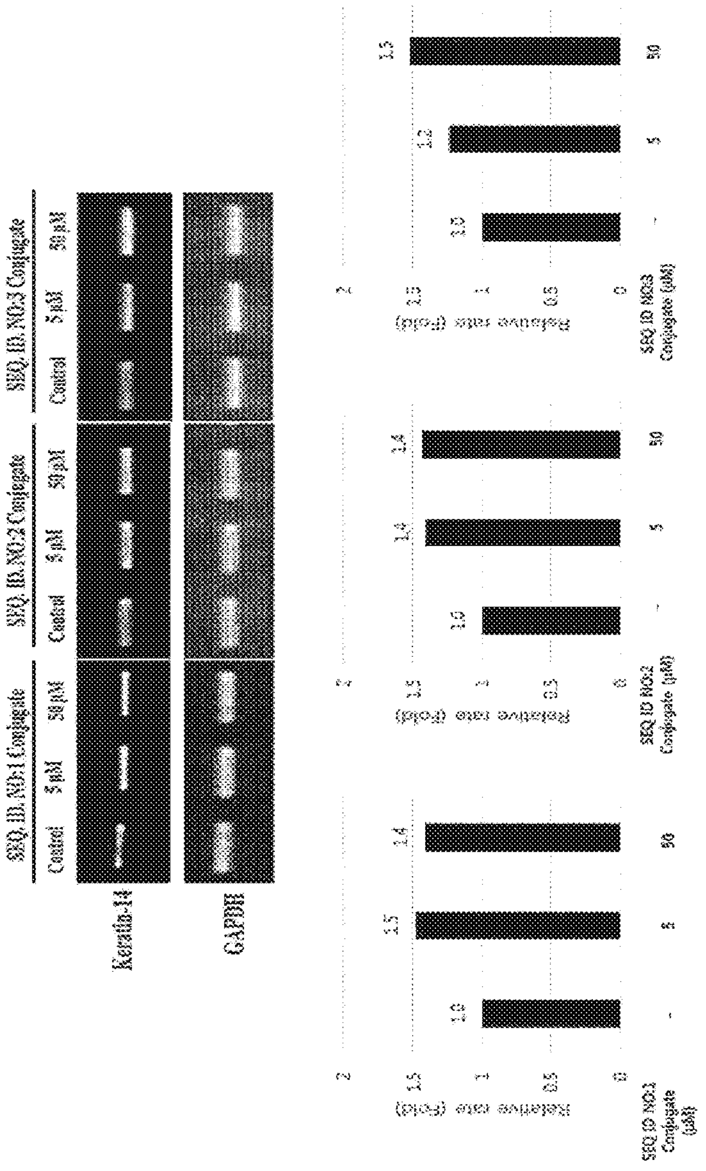

【Figure 13】
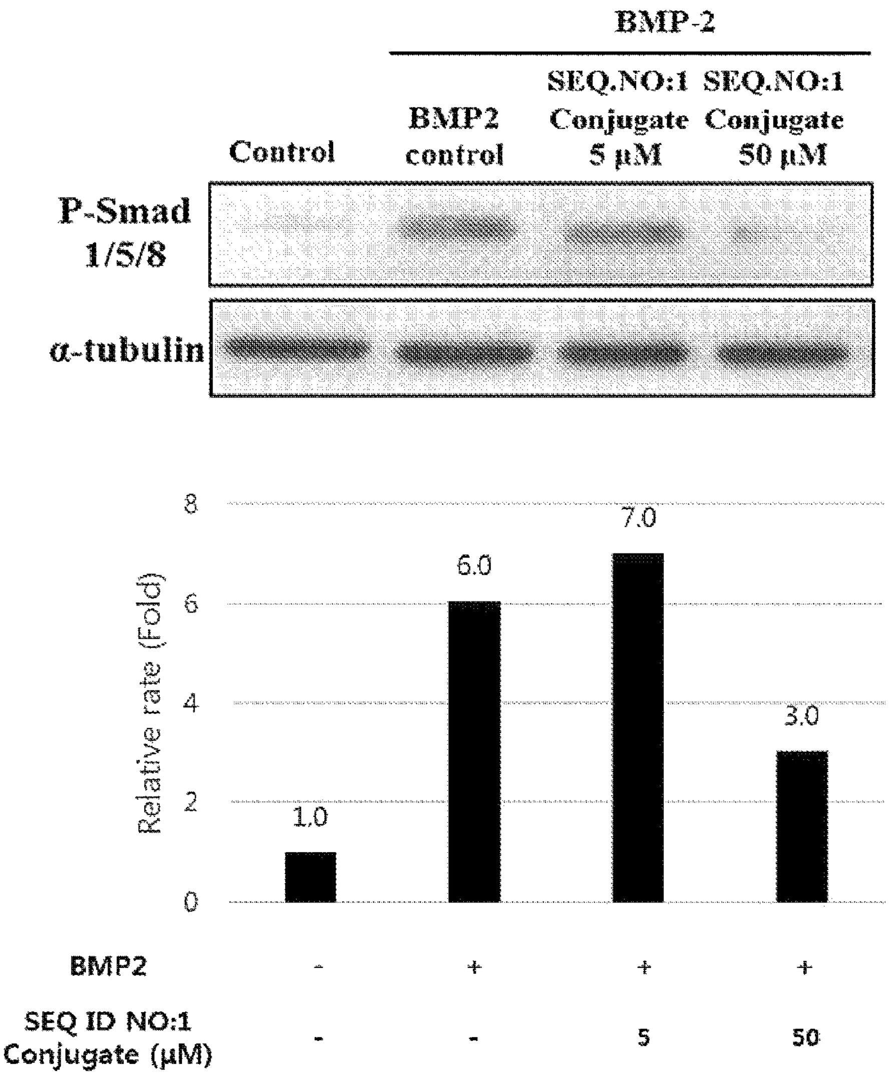

【Figure 14】
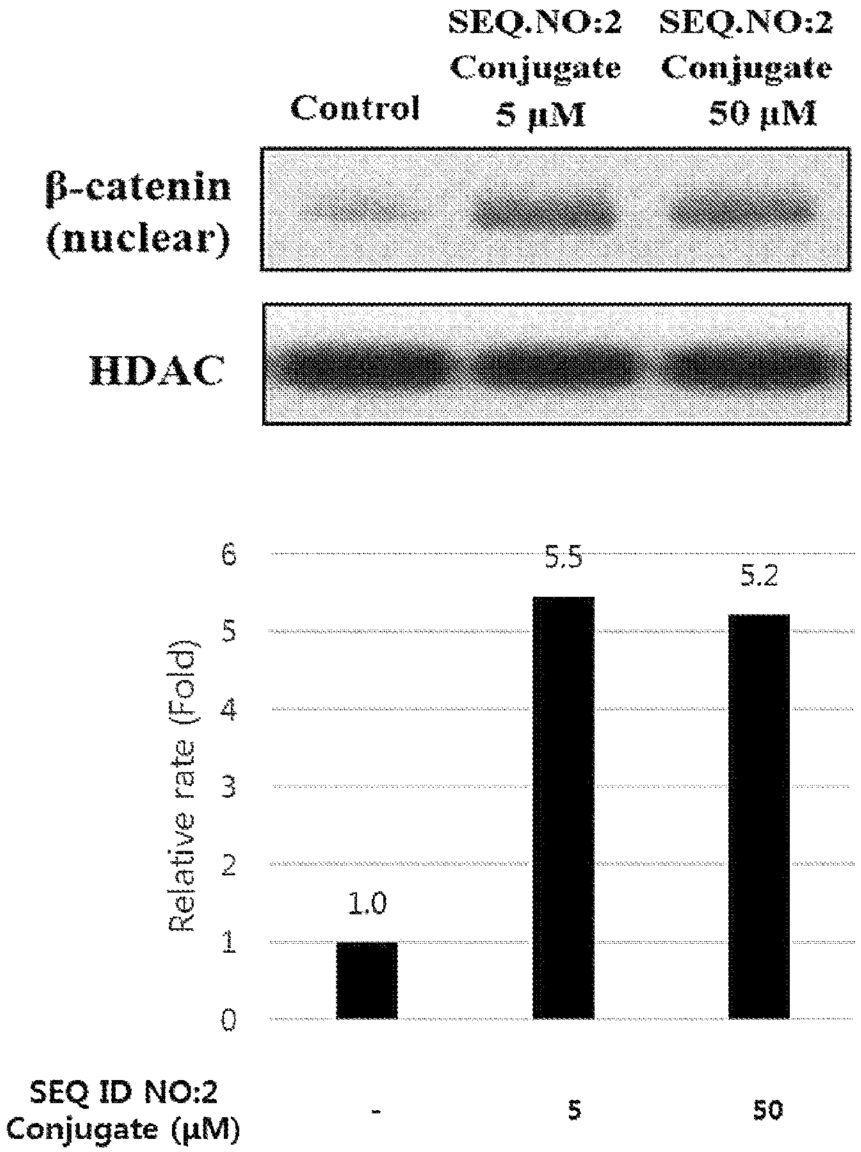

[Figure 15]
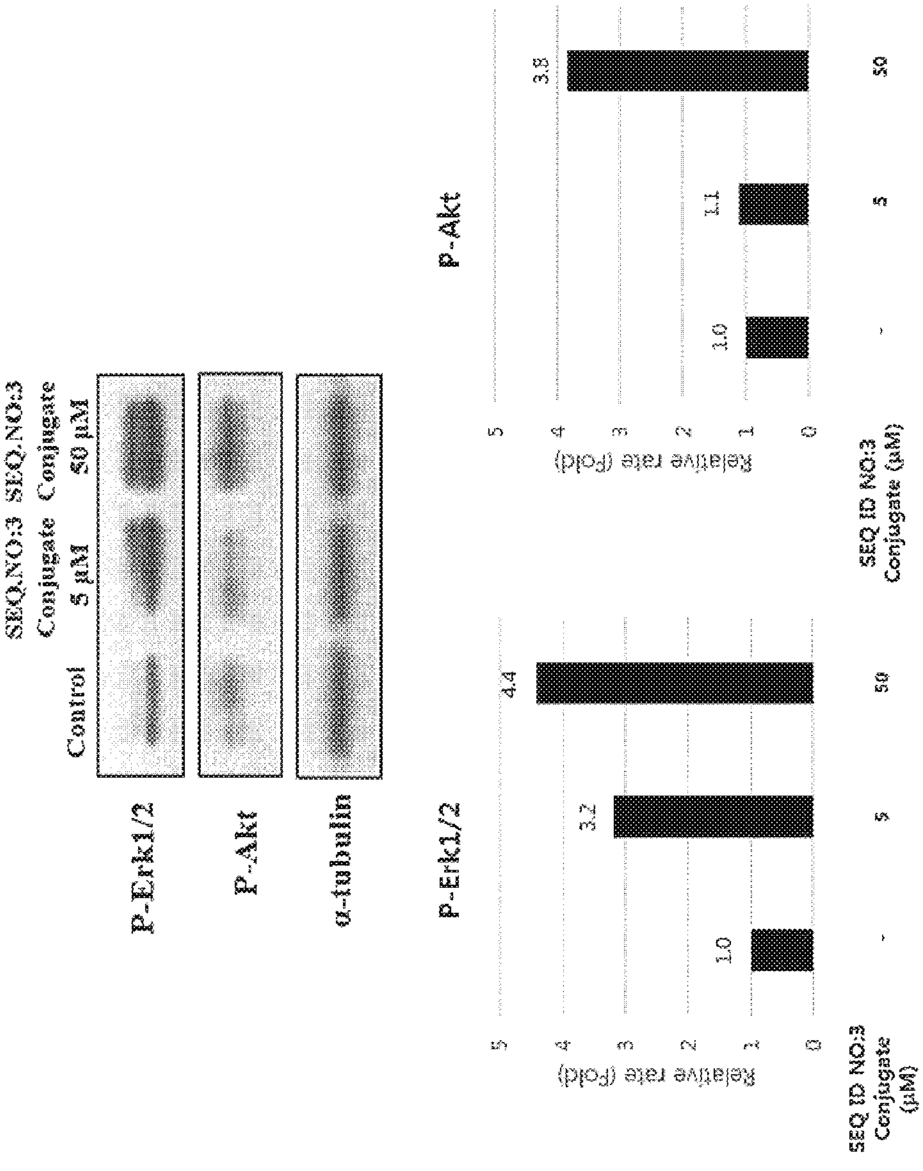

SEQUENCE LISTING

```
<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Peptide

<400> SEQUENCE: 1

Glu Leu Ile Glu His Gly Gly Gly Arg Pro Ala Asp
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Peptide

<400> SEQUENCE: 2

Arg Gln Thr Arg Val Gln Arg Cys His Cys
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: SITE
<222> LOCATION: (1)..(1)
<223> OTHER INFORMATION: N-terminal amino acid is acetylated

<400> SEQUENCE: 3

Tyr Lys Ser Lys Lys Gly Gly Trp Thr His
1               5                   10


<210> SEQ ID NO 4
<211> LENGTH: 20
<212> TYPE: DNA
<213> ORGANISM: Artificial Sequence
<220> FEATURE:
<223> OTHER INFORMATION: MSX2 forward primer

<400> SEQUENCE: 4

aacacaagac caaccggaag                                                   20


<210> SEQ ID NO 5
<211> LENGTH: 20
<212> TYPE: DNA
<213> ORGANISM: Artificial Sequence
<220> FEATURE:
<223> OTHER INFORMATION: MSX2 reverse primer

<400> SEQUENCE: 5

gcagccattt tcagcttttc                                                   20


<210> SEQ ID NO 6
<211> LENGTH: 24
<212> TYPE: DNA
<213> ORGANISM: Artificial Sequence
<220> FEATURE:
<223> OTHER INFORMATION: Keratin-14 forward primer

<400> SEQUENCE: 6
```

-continued

```
ccacctttca tcttcccaat tctc                                        24


<210> SEQ ID NO 7
<211> LENGTH: 18
<212> TYPE: DNA
<213> ORGANISM: Artificial Sequence
<220> FEATURE:
<223> OTHER INFORMATION: Keratin-14 reverse primer

<400> SEQUENCE: 7

gtgcggatct ggcggttg                                               18
```

TROLOX-PEPTIDE CONJUGATE AND USE THEREOF

CROSS-REFERENCE TO RELATED APPLICATIONS

This application is a National Stage Application of PCT/KR2020/005967, filed 6 May 2020, which claims benefit of Serial No. 10-2019-0053080, filed 7 May 2019 in Republic of Korea and which applications are incorporated herein by reference. To the extent appropriate, a claim of priority is made to each of the above disclosed applications.

SEQUENCE STATEMENT

This application contains a Sequence Listing, which has been submitted electronically in ASCII format and is hereby incorporated by reference in its entirety. Said ASCII copy, created and filed in U.S. Ser. No. 17/607,115, is named Sequence Listing 09983-0238FPWO.txt and is 4,096 bytes (4.00 KB) in size.

TECHNICAL FIELD

The present invention relates to a Trolox-peptide conjugate having a structure in which Trolox and a peptide are chemically bonded, and a use thereof.

BACKGROUND ART

The hair follicle is a unique organ present in mammalian skin and is an organ formed by growing and extending of the lower part of the primitive epidermis into a deeper skin layer. The plug of cells known as saccule or dermal papilla cells exists in the base of the hair follicle, and the dermal papilla cells are essential in normal circulation of the hair follicle and in growth of the hair shaft. The hair shaft has a thread-shaped structure formed by epithelial cells that are stems sprout over the scalp and composed of keratin filaments and filament-aggregating proteins tightly attached thereto.

Human hair periodically repeats an anagen phase for growing hair, a catagen phase for ending the growth and reducing a hair bulb, a telogen phase for stopping the action of dermal papilla and remaining hair on the scalp, and an exogen phase for beginning the action of dermal papilla or releasing new hair to induce old hair loss. The anagen phase is a period of growing hair and may be subdivided into a step of generating hair for hair getting out from the bulb to trichocyte and a step of forming hard keratin in hair follicle, and in this phase to the catagen phase, the hair grows consistently. The catagen phase is a period for ending the growth, maintaining the shape of hair and reducing a metabolic process, and in this phase, keratin is not formed. The hair corresponding to the catagen phase occupies 1% of total hair and corresponds to a state where cell division is suspended. The telogen phase corresponds to a period where dermal follicle shrinks, hair follicle contracts, and hair bulb is pushed up to loss hair.

Such hair is not an essential organ for conserving individual life but is the measure showing health conditions and an important part of the body, determining one's appearance. Accordingly, hair loss in daily life is regarded as natural physical activities for a normal person with a lot of hair, but for a person under losing his hair, corresponds to a factor which may severely affect mental health and the quality of life due to depression, shame, social isolation, or the like.

Recently, as the factors affecting the hair loss may include environmental factors such as climate, exposure to light or heat, and internal factors such as stress, disease, birth, hormone secretion and changes, taking medication, and nutritional status. However, the exact cause of the hair loss has not been found until now, and the population suffering from the hair loss increases according to the increase of stress due to the change of dietary life or social environments, the age is being lowered, and the population of women with hair loss is also increasing.

As a main hormone concerning the mechanism of hair loss, 5-alpha reductase (5-α reductase) may be shown. It has been reported that the 5-alpha reductase transforms testosterone which is one type of male hormone (androgen) into dihydrotestosterone (DHT), and the DHT produced thereby reduces the anagen phase of hair, increases the telogen phase, and kills follicle cells through involving cell signal transduction which induces follicle cell extinction.

Accordingly, in order to treat the cause of hair loss, Merck Co. developed Finasteride suppressing the generation of DHT by suppressing the activity of 5-alpha reductase and sells (U.S. Pat. No. 5,547,957 A). The Finasteride is convenient to take and is very effective, but reagents for preparing thereof are expensive or have toxicity and may burden the manufacturing cost. Particularly, the removal of a product incidentally produced is not easy, and the purity of a final product may be deteriorated. In addition, there are problems in that reagents or activity derivatives of which activity is easily inhibited by humidity are used, and mass production is difficult. Besides, research on promoting hair growth by promoting the growth of keratinocyte or vascular endothelium or suppressing the activity of proteins included in BMP, is being conducted (KR 2016-0023224 A). However, a medicine including a growth factor as an effective ingredient has very excellent efficacy, but on the contrary, there are problems in that an additional process and time are required for obtaining the growth factor of a natural form, a complicated purification process is required to removed contaminants derived from *E. coli* during a purification process, and since a molecular weight is large, the leaping over a protective layer of hair is not easy.

Accordingly, in order to solve the aforementioned problems, many studies have been conducted, and hair growth agents for preventing and treating hair loss have been suggested. However, the conventional hair growth agents do not have a function of preventing hair loss and promoting hair growth simultaneously, marked effects of treating hair loss and promoting hair growth are not shown substantially.

DETAILED DESCRIPTION OF THE INVENTION

Technical Problem

An object of the present invention is to provide a Trolox-peptide conjugate having very excellent effects of preventing hair loss or promoting hair growth.

Technical Solution

In order to accomplish the object, an aspect of the present invention is to provide a Trolox-peptide conjugate having a structure in which Trolox and a peptide are chemically bonded.

Also, another aspect of the present invention is to provide a pharmaceutical composition and a cosmetic composition, including a Trolox-peptide conjugate as an effective ingredient.

Advantageous Effects

According to the present invention, the Trolox-peptide conjugate not only suppressing the extinction of dermal papilla cells and keratinocyte and promoting the growth thereof and at the same time, having antioxidative effects, but also suppressing the activity of 5α-reductase very effectively, and hair loss may be controlled or prevented and at the same time, the growth of hair may be markedly promoted.

However, the effects of the present invention are not limited to the aforementioned effects, and it could be understood that unmentioned other effects are obvious to a person skilled in the art from the descriptions below.

BRIEF DESCRIPTION OF THE DRAWINGS

FIG. 1 to FIG. 3 show MASS analysis data on a conjugate of a peptide of SEQ ID NO: 1 and Trolox (conjugate of SEQ ID 1), a conjugate of a peptide of SEQ ID NO: 2 and Trolox (conjugate of SEQ ID 2), and a conjugate of a peptide of SEQ ID NO: 3 and Trolox (conjugate of SEQ ID 3) of the present invention.

FIG. 4 shows a graph confirming the cell proliferation promoting effects of human hair follicle dermal papilla cell (HFDPC).

FIG. 5 shows a graph confirming the cell proliferation promoting effects of HaCaT human keratinocyte.

FIG. 6 to FIG. 8 show graphs confirming inhibition effects of intracellular reactive oxygen species (ROC) in HFDPC.

FIG. 9 shows confirmed results of DKK-1 protein expression inhibition effects due to the suppression of the activity of 5α-reductase in HFDPC through western blot analysis.

FIG. 10 shows confirmed results of the expression change of a protein involving apoptosis in HFDPC through western blot analysis.

FIG. 11 shows confirmed results of the expression change of a MSX2 gene in human hair germinal matrix cell (HHGMC) through PCR.

FIG. 12 shows confirmed results of the expression change of a Keratin-14 gene in HaCaT through PCR.

FIG. 13 shows confirmed results of the expression inhibition effects of P-smad 1/5/8 which is a cell signal transduction protein involving BMP-2 in a HFDPC cell through western blot analysis.

FIG. 14 shows confirmed results of the position degree of β-catenin in a nucleus, which is a cell signal transduction protein involving WNT in a HFDPC cell through western blot analysis.

FIG. 15 shows confirmed results of the expression increasing effects of p-Erk 1/2 and p-Akt, which are cell signal transduction proteins involving KGF in a HFDPC cell through western blot analysis.

BEST MODE FOR CARRYING OUT THE INVENTION

Hereinafter, the present invention will be described in detail.

1. Trolox-Peptide Conjugate

An aspect of the present invention provides a Trolox-peptide conjugate.

The Trolox of the present invention is 6-hydroxy-2,5,7,8-tetramethylchromane-2-carboxylic acid and has a structure represented by Formula 1 below.

[Formula 1]

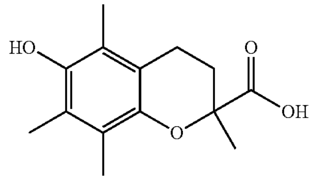

The conjugate of the present invention has a structure in which Trolox and a peptide are chemically bonded.

Through the bonding of the Trolox and the peptide as described above, the solubility of the Trolox which has poor solubility in water may be markedly increased, the activity of 5α-reductase may be very effectively suppressed, the extinction of papilla cells and keratinocyte may be suppressed and promoted, and accordingly, effects of avoiding or preventing hair loss and promoting hair growth may be achieved at the same time.

The peptide means a linear molecule formed by the bonding of amino acids from each other by a peptide bond. The formation of the peptide may be achieved by a common biological or chemical synthetic methods known in the art, and may be achieved by, for example, a method such as solid-phase synthesis techniques.

The peptide may be composed of 5 to 30, preferably, 8 to 20, more preferably, 10 to 15 amino acids. If the number of amino acids forming the peptide is less than 5, the solubility of Trolox in water may not be significantly increased, and if the number of amino acids forming the peptide is greater than 30, the size of the peptide is excessively large, and there may be problems of degrading the absorption for achieving desired medical effects.

The peptide may have a ratio of side chain-containing amino acids which may show hydrophilicity of 50% to 100%, for example, 80% to 100%, and the peptide may have a ratio of side chain-containing amino acids which may show hydrophobicity of 0% to 50%, for example, 0% to 20%. If the ratio of the side chain-containing amino acids which may show hydrophilicity deviates from the aforementioned range, effects of significantly increasing the solubility of the Trolox in water may not be shown.

The side chain-containing amino acid which may show hydrophilicity may be selected from the group consisting of arginine (Arg), histidine (His), lysine (Lys), aspartic acid (Asp), glutamic acid (Glu), serine (Ser), threonine (Thr), asparagine (Asn), glutamine (Gln), cysteine (Cys), selenocysteine (Sec), glycine (Gly) and proline (Pro), and the side chain-containing amino acid which may show hydrophobicity may be selected from the group consisting of alanine (Ala), valine (Val), isoleucine (Ile), leucine (Leu), methionine (Met), phenylalanine (Phe), tyrosine (Tyr) and tryptophan (Trp).

The peptide may be formed by bonding at least 50% or more of the side chain-containing amino acids which may show hydrophilicity from each other by a peptide bond, and may be a water-soluble peptide.

The peptide includes at least one amino acid sequence among SEQ ID NO: 1 to SEQ ID NO:3.

The peptide composed of the amino acid sequence of SEQ ID NO: 1 may suppress the expression of genes DKK1, BMP4 and TGF-β involving the induction of hair loss and may prevent hair loss.

The peptide composed of the amino acid sequence of SEQ ID NO: 2 is a peptide having a similar function as a growth factor encouraging the period of hair, and by the peptide, the intranuclear translocation of R-catenin may be induced to finally let mother cells newly grow, thereby degrading the function of dihydrotestosterone (DHT) due to male hormone and contributing to the prevention of hair loss.

The peptide composed of an amino acid sequence of SEQ ID NO:3 induces new blood vessel formation and maintains healthy and thick hair to contribute to the prevention of hair loss.

In the Trolox-peptide conjugate of the present invention, Trolox and a peptide are conjugated, and the inherent functions of preventing hair loss and promoting hair growth of a peptide may be maintained and further, markedly improved effects of preventing hair loss and promoting hair growth may be achieved when compared to a case of using Trolox or a peptide solely.

The amino acids of SEQ ID NO: 1 to SEQ ID NO: 3 may be the variants or fragments of amino acids having different sequences by the deletion, insertion, substitution or combinations thereof of amino acid residues, within a range not influencing the increase of the solubility in water through the bonding of the peptide to Trolox, and in some cases, may be transformed by phosphorylation, sulfation, acrylation, glycosylation, methylation, farnesylation, or the like. In addition, the amino acids of SEQ ID NO: 1 to SEQ ID NO: 3 include a peptide having substantially the same amino acid sequences as the peptide including the amino acid sequences of SEQ ID NO: 1 to SEQ ID NO: 3, and the variants or active fragments thereof.

The peptide including substantially the same amino acid sequence means a peptide having amino acid sequence having a sequence homology of 75% or more, preferably, 80% or more, more preferably, 90% or more, most preferably, 95% or more as the amino acid sequence of the SEQ ID NO: 1.

In order to provide the peptide with chemical stability, enforced pharmacological properties (half-life, absorbency, titer, efficacy, or the like), changed specificity (for example, a wide range of biological active spectrum), reduced antigenicity, to the N-terminal or C-terminal of the peptide a protecting group such as an acetyl group, fluorenyl methoxy carbonyl group, formyl group, palmitoyl group, myristyl group, stearyl group and polyethylene glycol (PEG) may be additionally bonded.

The chemical stability of the peptide includes both the meaning of a storage stability (for example, storage stability at room temperature) as well as stability "in vivo", protecting the peptide from the attack of a protein cleaving enzyme "in vivo".

2. Composition for Preventing Hair Loss and Promoting Hair Growth, Including Trolox-Peptide Conjugate as an Effective Ingredient Another aspect of the present invention provides a composition for preventing hair loss and promoting hair growth, including a Trolox-peptide conjugate as an effective ingredient.

The composition of the present invention includes the Trolox-peptide conjugate explained in the item of "1. Trolox-peptide conjugate" as an effective ingredient and may be used as the use of preventing hair loss and promoting hair growth, and this invokes the explanation in the item of "1. Trolox-peptide conjugate". Hereinafter, unique configurations of the composition for preventing hair loss and promoting hair growth will be explained.

The "hair loss prevention" has the meaning including the suppression of the falling out or reduction of hair, and "hair growth promotion" has the meaning of promoting the growth of hair.

The composition may be provided in a pharmaceutical composition or a cosmetic composition type, without limitation.

The pharmaceutical composition may be carried in a pharmaceutically acceptable carrier such as a colloidal suspension, a powder, a saline solution, a lipid, liposomes, microspheres, and nano spherical particles. These may form a conjugate or be involved with a carrying means and may be carried in vivo using a carrying system well-known in the art such as a lipid, liposomes, minute particles, gold, nanoparticles, a polymer, a condensate reactant, polysaccharides, a polyamino acid, dendrimers, saponins, an adsorption enhancing substance and a fatty acid.

The pharmaceutically acceptable carrier in the Trolox-peptide conjugate may include those commonly used during the preparation of formulations, and include lactose, dextrose, sucrose, sorbitol, mannitol, starch, acacia, rubber, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oils and the like.

The pharmaceutical composition may further include lubricants, wetting agents, sweetening agents, flavoring agents, emulsifying agent, suspending agents, preservatives, and the like in addition to the above components.

The pharmaceutical composition may be administered orally or parenterally (for example, intramuscular, intravenous, intraperitoneal, subcutaneously, intradermal, or locally), and the dosage is dependent on the state, weight, and the degree of disease of a patient, a medicine type, and the route and duration of administration, but may be suitably selected by a person skilled in the art.

The pharmaceutical composition of the present invention is administered in a pharmaceutically effective amount. In the present invention, the "pharmaceutically effective amount" refers to an amount sufficient to treat diseases in a reasonable benefit/danger ratio applicable for medical treatment. The effective dosage degree may be determined according to factors including the type of disease and severity of a patient, the activity of a medicine, sensitivity to a medicine, administration time, administration route and discharge ratio, the duration of treatment and medicines used simultaneously, and other factors well-known in a medical field. The pharmaceutical composition may be administered as an individual treatment or administered together with other obesity treatment, simultaneously, separately, or in order, and may be administered as a single dose or multiple doses. Considering all the factors, it is important to administer an amount capable of obtaining maximum effects with a minimum amount without side effects, and this may be easily determined by a person skilled in the art.

The effective amount of the pharmaceutical composition may be changed according to the age, sex, state, weight, the absorbency of an active ingredient in vivo, an inactivation rate, a excretion speed, a disease type, and a medicine used together, and may be increased or decreased according to the route of administration, the severity of obesity, sex, weight, age, or the like. For example, the pharmaceutical composition may be administered in about 0.0001 μg to 500 mg, preferably, 0.01 μg to 100 mg per 1 kg of a patient's weight per day.

The cosmetic composition may be formed in an arbitrary formulation commonly prepared in this technical field, and may be formulated in, for example, solutions, suspensions, emulsions, pastes, gels, creams, lotions, powders, soaps, surfactant-containing cleansing, oils, powder foundations, emulsion foundations, wax foundations, and sprays, but are not limited thereto.

The cosmetic composition may be prepared in various forms, for example, emollient beauty washes, nutrition beauty washes, nutrition creams, massage creams, essences, eye creams, cleansing creams, cleansing foams, cleansing waters, packs, sprays, powders, hair tonics, hair creams, hair lotions, hair shampoos, hair rinses, hair conditioners, hair sprays, hair air-sols, pomades, solutions such as gel, sol-gels, emulsions, oils, waxes, or air-sols, but are not limited thereto.

In the case where the formulation of the cosmetic composition is a paste, cream or gel, animal oil, vegetable oil, wax, paraffin, starch, tragacanth, cellulose derivative, polyethylene glycol, silicon, bentonite, silica, talc or zinc oxide, or the like may be used as a carrier component.

In the case where the formulation of the cosmetic composition is a powder or spray, lactose, talc, silica, aluminum hydroxide, calcium silicate or polyamide powder may be used as a carrier component, and particularly, in the case of spray, a propellant such as chlorofluorohydrocarbon, propane/butane or dimethyl ether may be additionally included, but is not limited thereto.

In the case where the formulation of the cosmetic composition is a solution or emulsion, a solvent, a solubilizer or an emulsifier may be used as a carrier component, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, fatty acid ester of sorbitan, or the like may be used.

In the case where the formulation of the cosmetic composition is a suspension, a diluent of a liquid phase such as water, ethanol and propylene glycol, a suspending agent such as ethoxylated isostearyl alcohol, polyoxyethyl sorbitol ester and polyoxyethylene sorbitan ester, microcrystalline cellulose, aluminum metahydroxide, bentonite, agar, tragacanth, or the like may be used.

In the case where the formulation of the cosmetic composition is a surfactant-containing cleansing, aliphatic alcohol sulfates, aliphatic alcohol ether sulfates, sulfosuccinic acid monoesters, isethionates, imidazolinium derivatives, methyl taurates, sarcosinates, fatty acid amide ether sulfates, alkyl amido betaines, aliphatic alcohols, fatty acid glycerides, fatty acid diethanolamides, vegetable oils, lanoline derivatives, ethoxylated glycerol fatty acid esters, or the like may be used as a carrier component.

In the case where the formulation of the cosmetic composition is a hair shampoo, base components for forming the shampoo, such as thickeners, surfactants, viscosity adjusting agents, moisturizers, pH adjusting agents, antiseptics, and essential oils may be mixed with the Trolox-peptide conjugate of the present invention. CDE may be used as the thickener, the surfactant may be LES which is an anionic surfactant and cocobetaine which is an amphoteric surfactant, the viscosity adjusting agent may be Polyquater, the moisturizer may use glycerin, and the pH adjusting agent may use citric acid or sodium hydroxide. The antiseptic may be a grapefruit extract, and in addition, essential oils such as cedarwood, peppermint and rosemary, silk amino acid, pentanol, and vitamin E may be added.

The components included in the cosmetic composition may include, in addition to the Trolox-peptide conjugate of the present invention and carrier components, components commonly used in cosmetic compositions, for example, conventional adjuvants such as antioxidants, stabilizers, solubilizers, vitamins, pigments, and perfumes, as effective ingredients, but are not limited to.

Hereinafter, the present invention will be described in detail with reference to Examples and Experimental Examples.

However, the Examples and Experimental Examples below are provided only for illustrating the present invention, and the contents of the present invention are not limited by the Examples and Experimental Examples below.

Preparation Example 1

Synthesis of Peptide

[1-1] Synthesis of Peptide Including Amino Acid Sequence of SEQ ID NO: 2

700 mg of a chlorotrityl chloride resin (CTL resin, Nova biochem [0064] Cat No. 01-64-0021) was placed in a reaction vessel, and 10 ml of methylene chloride was added to the reaction vessel, followed by stirring for 3 minutes. Then, the solvent was removed, and 10 ml of dimethyl formamide was added thereto. After additionally stirring for 3 minutes, the solvent was removed. 10 ml of dichloromethane was added to the reaction vessel, and after adding 200 mmole of Fmoc-Cys(trt)-OH (Bachem, Swiss) and 400 mmole of diisopropylethylamine, stirring was performed for 1 hour for inducing the reaction. After washing the reaction product, methanol and diisopropylethylamine mixed in a ratio of 2:1 were added, and reaction was performed for 10 minutes. Then, dichloromethane and dimethylformamide mixed in a ratio of 1:1 were added in an excessive amount, and washing was performed again. Then, the solvent was removed, and 10 ml of dimethylformamide was added thereto, followed by stirring for 3 minutes, and removing the solvent. After that, a process including adding 10 ml of a deprotection solution (20% piperidine/dimethylformamide) to the reaction vessel for deprotection reaction, stirring for 10 minutes at room temperature, and then removing the solvent, was conductive total two times. After that, the solvent was removed, and the resultant product was washed with dimethylformamide twice, with methylene chloride twice, and with dimethylformamide once for 3 minutes each to obtain a Cys(trt)-CTL resin.

To a new reaction vessel, 10 ml of a DMF solution was added, 200 mmole of Fmoc-His(trt)-OH (Bachem, Swiss), 200 mmole of hydroxylbenzotriazole (HOBt) and 200 mmole of benzotriazol-1-yloxytris(dimethylamino)phosphonium hexafluorophosphate (Bop) were added and stirred. 400 mmole of diisopropylethylamine was added to the reaction vessel in two portions and then stirred for at least 5 minutes until all solid state reactants were dissolved. Then, the solution thus obtained was put in the reaction vessel containing the Cys(trt)-CTL resin and stirred at room temperature for 1 hour. After that, all solvents were removed, washing with dimethylformamide was performed three times for 5 minutes each, and the reaction degree of the reactants was checked through a kaiser test (ninhydrin test). Then, a His(trt)-Cys(trt)-CTL resin was prepared by performing deprotection reaction with respect to the reaction product, which was performed during the preparation process of the Cys(trt)-CTL resin. After thoroughly washing with dimethylformamide and methylene chloride, the reaction degree was checked through a kaiser test.

Then, chain reaction was performed with the His(trt)-Cys (trt)-CTL resin in the order of Fmoc-Cys(trt), Fmoc-Arg, Fmoc-Gln(trt), Fmoc-Val, Fmoc-Arg, Fmoc-Thr, Fmoc-Gln (trt) and Fmoc-Arg(pbf). After that, the Fmoc-protecting group was removed by reacting with a deprotection solution twice for 10 minutes and then washing well. The deprotected resin, acetic anhydride, diisopropylethylamine and HOBt were reacted for one hour to perform acetylation reaction. Then, the resultant product was washed with dimethylformamide, methylene chloride and methanol three times each, a nitrogen gas was slowly flowed to dry, and then thorough drying was performed under $P_2O_5$ in vacuum under a reduced pressure.

To the dried reaction product, 30 ml of a trifluoroacetic acid solution (95% of TFA, 2.5% of distilled water, and 2.5% of thioanisole) was added and reacted by stirring for 2 hours at room temperature. A resin obtained by completing the reaction was filtered using a filter and washed with a small amount of trifluoroacetic acid, and the washed solution was combined with the mother liquor. The pressure of the mixture solution was reduced, and distillation was performed until the total volume remained about half, and 50 ml of cold ether was added to induce precipitation. The precipitates were collected using a centrifuge and washed with cold ether two times. Then, the mother liquor was removed and drying was sufficiently performed under nitrogen to synthesize 0.65 g of a crude $NH_2$-Arg-Gln-Thr-Arg-Val-Gln-Arg-Cys-His-Cys-OH peptidyl resin (SEQ ID NO: 2) (Yield: 92.6%). The molecular weight of a peptide including an amino acid sequence of SEQ ID NO: 2 was measured using a molecular weight analyzer, and as a result, it was confirmed that the molecular weight corresponded to 1287.1 Da (calculated value: 1286.5 Da).

[1-2] Synthesis of Peptide Including Amino Acid Sequences of SEQ ID NO: 1 and SEQ ID NO: 3

Peptides including the amino acid sequences of SEQ ID NO: 1 and SEQ ID NO: 3 were synthesized by the same method as the synthetic method of [1-1] above. In this case, chain reaction was performed with the CTL resin with Fmoc-Asp(OtBu), Fmoc-Ala, Fmoc-Pro, Fmoc-Arg (Pbf), Fmoc-Gly, Fmoc-Gly, Fmoc-Gly, Fmoc-His(Trt), Fmoc-Glu (OtBu), Fmoc-Ile, Fmoc-Leu and Fmoc-Glu(OtBu) in order to synthesize a peptide including the amino acid sequence of SEQ ID NO: 1, and chain reaction was performed with the CTL resin with Fmoc-His(Trt), Fmoc-Thr(tBu), Fmoc-Trp, Fmoc-Gly, Fmoc-Gly, Fmoc-Lys(Boc), Fmoc-Lys(Boc), Fmoc-Ser(tBu), Fmoc-Lys(Boc) and Fmoc-Tyr(tBu) in order, and acetylated to synthesize a peptide including the amino acid sequence of SEQ ID NO: 3.

TABLE 1

| SEQ ID NO | Amino acid sequence |
|---|---|
| 1 | Glu-Leu-Ile-Glu-His-Gly-Gly-Gly-Arg-Pro-Ala-Asp |
| 2 | Arg-Gln-Thr-Arg-Val-Gln-Arg-Cys-His-Cys |
| 3 | Ac-Tyr-Lys-Ser-Lys-Lys-Gly-Gly-Trp-Thr-His |

[Preparation Example 2] Preparation of Trolox-Peptide Conjugate 1 mole of a peptidyl resin and 10 mL of 1-methyl-2-pyrrolidinone (NMP) were placed in a peptide reactor, and 270 mg (2.0 equiv.) of 1-hydroxybenzotriazole (1-HOBt) and 759 mg (2.0 equiv.) of N,N,N',N'-tetramethyl-O-(1H-benzotriazol-1-yl)uronium hexafluorophosphate (HBTU) were added thereto, followed by reacting for 30 minutes. Then, to the reaction product, 388 mg (3.0 equiv.) of N,N'-diisopropylethylamine (DIEA) and 500 mg (2.0 equiv.) of Trolox were added and reacted at room temperature for 72 hours, and filtering was conducted. Then, the filtrate and a cleavage solution were reacted at room temperature for 2 hours to remove a resin and a protecting group. Finally, 10 mL of diethyl ether was added to crystallize and to prepare a Trolox-peptide conjugate (i.e., a conjugate of a peptide of SEQ ID NO: 1, SEQ ID NO: 2 or SEQ ID NO: 3 with Trolox). Reaction for preparing the Trolox-peptide conjugate is as Reaction 1 below.

[Reaction 1]

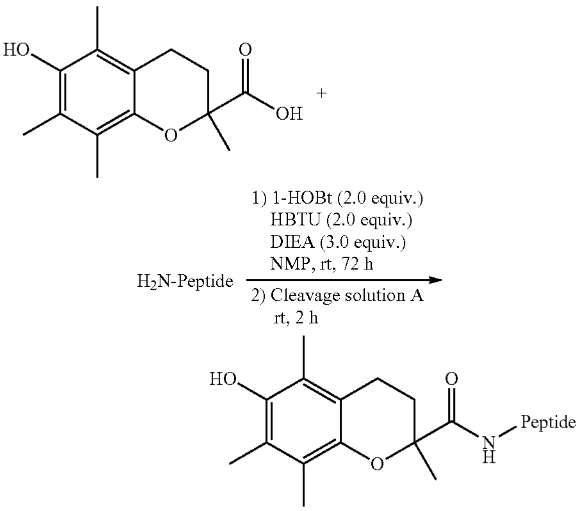

MASS analysis data on the three types of the Trolox-peptide conjugates thus produced are shown in FIG. 1 to FIG. 3, respectively. In the MASS analysis data, it could be clearly confirmed that the Trolox-peptide conjugates of SEQ ID NO: 1 to SEQ ID NO: 3 corresponding to 1550.7 Da, 1487.62 Da, and 1423.6 Da were synthesized.

Example 1

Confirmation of Proliferation Promoting Effects

Human hair follicle dermal papilla cells (HFDPC) and HaCaT which is human keratinocyte were dispensed by $2\times10^3$ in each well of a 96-well plate and cultivated overnight. The medium of the cultivated cells was replaced with a serum-free medium, and treatment with Trolox-peptide conjugates of 0.5 μM, 5 μM or 50 μM were performed, and additional cultivation was performed for 3 days. Then, in order to confirm the proliferation of the cells, 4 mg/ml of 3-(4,5-dimethylthiazol-2-yl)-2,5-diphenyltetrazolium bromide (MTT) was put to the wells by 100 μl each and reacted for 4 hours. Formazan thus produced was treated with DMSO and dissolved, and light absorbance at 560 nm was measured using a microplate reader. In this case, as a positive control, 1 μM of IGF-1 or EGF, which is known as a growth factor promoting the proliferation of HFDPC and HaCaT cells was used, and as a comparison group, single compounds of Trolox and a peptide having the amino acid sequences of SEQ ID NO: 1 to SEQ ID NO: 3, having the same amounts as the Trolox-peptide conjugate of the present invention, were used.

As a result, as shown in FIG. 4 and FIG. 5, in the case of treating the HFDPC and HaCaT cells with the Trolox-peptide conjugates, it was confirmed that all showed cell proliferation, and such effects of increasing cell proliferation was confirmed to increase further with the increase of the concentration of the Trolox-peptide conjugate treated. Particularly, in the case of treating HaCaT with 50 μM of the Trolox-peptide (SEQ ID NO: 2) conjugate, it was confirmed that the cell proliferation was significantly increased to the degree of EGF positive control. On the contrary, the Trolox compound used as the comparison group rarely showed cell proliferation effects, and the peptide compounds having the amino acid sequences of SEQ ID NO: 1 to SEQ ID NO: 3 showed weak cell proliferation effects or lower cell proliferation effects than the same amount of the Trolox-peptide conjugate.

From the results, it could be found that if treated with the Trolox-peptide conjugate, hair growth promoting effects may be shown by promoting the proliferation of HFDPC and HaCaT cells.

Example 2

Confirmation of Intracellular Reactive Oxygen Species (ROS) Inhibition Effects

HFDPCs were dispensed by $3\times10^5$ in each well of a 6-well plate and cultivated overnight. 50 mJ of UVB was irradiated to the cultivated cells, the medium of the cells was replaced with a serum-free medium, treatment with a Trolox-peptide conjugate of 5 μM or 50 μM was performed, and additional cultivation was performed for 24 hours. Then, in order to measure the intracellular ROS concentration, treatment with dichlorofluorescin diacetate (DCFH-DA) was performed, reaction was performed for 30 minutes, cells were recovered, and the change of an average FL1 values was confirmed using FACS. In this case, as a positive control, 5 mM of N-acetyl-L-cysteine (NAC) which is known to have intracellular ROS inhibition effects was used.

As a result, as shown in FIG. 6 to FIG. 8, it was confirmed that, if treated with the Trolox-peptide conjugate, intercellular ROS increased by the irradiation of UVB was inhibited to a similar degree as that of the positive control.

From the results above, it could be found that if treated with the Trolox-peptide conjugate, the intracellular ROS was inhibited, intracellular oxidative stress in dermal papilla cells was significantly reduced, and preventing effects of hair loss may be shown.

Example 3

Confirmation of Expression Suppressing Effects of DKK1 Protein

Dihydrotestosterone (DHT) produced from testosterone by 5α-reductase is known to induce the increase of the expression of DKK1 which is a protein inducing hair loss. Accordingly, the suppression of the expression of DKK1 or not by the Trolox-peptide (SEQ ID NO: 2) conjugate was confirmed.

HFDPCs were dispensed by $3\times10^5$ in each well of a 6-well plate and cultivated overnight. The medium of the cultivated cells was replaced with a serum-free medium, treatment with a Trolox-peptide (SEQ ID NO: 2) conjugate of 5 μM or 50 μM, a mouse liver extract including 5α-reductase and testosterone was performed, and additional cultivation was performed for 24 hours. Then, the aspect of protein expression was confirmed using a specific antibody to the DKK-1 protein (Santacruz biotechnology, USA) by performing western blot.

As a result, as shown in FIG. 9, the expression of the DKK1 protein was increased by the treatment with the testosterone and mouse liver extract, and in the case of being treated with the Trolox-peptide (SEQ ID NO: 2) conjugate, it was confirmed that the expression of the increased DKK1 protein was reduced.

From the results above, it could be found that the Trolox-peptide conjugate suppresses the production of DHT by suppressing the activity of 5α-reductase, and at last, the expression of the DKK1 protein inducing hair loss may be suppressed very effectively.

Example 4

Confirmation of Protein Expression Change Involving Cell Death

HFDPCs were dispensed by $3\times10^5$ in each well of a 6-well plate and cultivated overnight. The medium of the cultivated cells was replaced with a serum-free medium, treatment with Trolox of 50 μM, a Trolox-peptide (SEQ ID NO: 2) conjugate of 50 μM, or a Trolox-peptide (SEQ ID NO: 3) conjugate of 50 μM, was performed for each, and additional cultivation was performed for 24 hours. Then, protein expression change was confirmed by performing western blot using a specific antibody to Bcl-2 and Bax proteins (Santacruz biotechnology, USA).

As a result, as shown in FIG. 10, it was confirmed that, if treated with only Trolox, no change was found for the expression of Bcl-2, and the expression of Bax was increased. On the contrary, in the cases of treating with the Trolox-peptide (SEQ ID NO: 2) conjugate and the Trolox-peptide (SEQ ID NO: 3) conjugate, the expression of Bcl-2 was increased, and the expression of Bax was significantly reduced.

From the results above, it could be found that if the Trolox was used solely, the cell death could not be induced, but if the peptide was bonded to Trolox, the cell death could be induced by inducing the expression change of a protein involving the cell death.

Example 5

Confirmation of Expression Increase of MSX2 Gene

In human hair germinal matrix cells (HHGMC), the change of the expression of a MSX2 gene involving hair follicle development, the hair cycle control, and hair shaft eruption by the Trolox-peptide conjugate was confirmed.

HHGMCs were dispensed by $3\times10^5$ in each well of a 6-well plate and cultivated overnight. The medium of the cultivated cells was replaced with a medium containing 0.5% of a fetal bovine serum, treatment with a Trolox-peptide (SEQ ID NO: 1) conjugate, a Trolox-peptide (SEQ ID NO: 2) conjugate, or a Trolox-peptide (SEQ ID NO: 3) conjugate of 5 μM or 50 μM, was performed, respectively, and additional cultivation was performed for 24 hours. Then, total RNA was extracted from the cells and quantified using a cDNA synthesis kit (Intron, Korea), and cDNA was synthesized from the same amount of the total RNA. By using the primer of Table 2 below with the synthesized cDNA as a template, PCR reaction was performed with respect to a MSX2 gene. After that, electrophoresis was performed with respect to the PCR product in 5% (w/v) agarose gel, and the degree of expression of the MSX2 gene was compared.

TABLE 2

| SEQ ID NO | Direction | Primer sequence (5'→3') |
|---|---|---|
| 4 | Forward direction | AACACAAGACCAACCGGAAG |
| 5 | Reverse direction | GCAGCCATTTTCAGCTTTTC |

As a result, as shown in FIG. 11, it was confirmed that the expression of the MSX2 gene was increased if treated with the Trolox-peptide conjugate. From the results above, it could be found that the expression of the MSX2 gene involving hair follicle development, the control of hair cycle and hair shaft eruption was increased by the Trolox-peptide conjugate, and hair loss could be prevented.

Example 6

Confirmation of Expression Increase of Keratin-14 Gene

HaCaT cells were dispensed by $5\times10^5$ in each well of a 6-well plate and cultivated overnight. The medium of the cultivated cells was replaced with a serum-free medium, treatment with a Trolox-peptide (SEQ ID NO: 1) conjugate, a Trolox-peptide (SEQ ID NO: 2) conjugate or a Trolox-peptide (SEQ ID NO: 3) conjugate of 5 μM or 50 μM, was performed, respectively, and additional cultivation was performed for 24 hours. Then, the degree of expression of the Keratin-14 gene was compared by the same process as in [Example 5].

TABLE 3

| SEQ ID NO | Direction | Primer sequence (5'→3') |
|---|---|---|
| 6 | Forward direction | CCACCTTTCATCTTCCCAATTCTC |
| 7 | Reverse direction | GTGCGGATCTGGCGGTTG |

As a result, as shown in FIG. 12, it was confirmed that the expression of the Keratin-14 gene was increased if treated with the Trolox-peptide conjugate. Such increasing effects of the expression of the Keratin-14 gene were confirmed to increase with the increase of the concentration of the Trolox-peptide conjugate for treatment. From the results above, it could be found that the expression of the keratin-14 gene was increased by the Trolox-peptide conjugate, and hair growth could be promoted.

Example 7

Confirmation of Cell Signal Transduction Effects

It has been reported that there are signal transduction of Wnt, Shh, BMP, or the like, controlling a hair follicle cycle. Accordingly, the effects of suppressing (or preventing) hair loss or promoting hair growth were shown by confirming what cell signal transduction was involved by the Trolox-peptide conjugates.

HFDPCs were dispensed by $3\times10^5$ in each well of a 6-well plate and cultivated overnight. The medium of the cultivated cells was replaced with a serum-free medium, and the experiments below were performed.

[7-1] Suppressing Effects of Bone Morphogenetic Protein (BMP)2 Cell Signal Transduction The HFDPC cells were treated with 50 ng/μl of BMP-2 and a Trolox-peptide (SEQ ID NO: 1) conjugate of 5 μM or 50 μM, and additionally cultivated for 15 minutes. Then, western blot was performed using a specific antigen to a P-smad 1/5/8 protein which is a subprotein of which expression is controlled by BMP2 cell signal transduction (Cell signaling, USA), and the expression change of a protein was confirmed.

As a result, as shown in FIG. 13, in the case of treating with the Trolox-peptide (SEQ ID NO: 1) conjugate of 50 μM, it was confirmed that the level of expression of the P-smad 1/5/8 protein increased by the treatment with BMP2 was reduced.

From the results above, it could be found that the BMP2 cell signal transduction inducing hair loss was suppressed by the Trolox-peptide (SEQ ID NO: 1) conjugate, and the hair loss could be effectively suppressed or prevented.

[7-2] Cell Signal Transduction Effects of Trolox-Peptide Conjugate

The HFDPC cells were treated with a Trolox-peptide (SEQ ID NO: 2) conjugate of 5 μM or 50 μM, and additionally cultivated for 30 minutes. Then, the cells were recovered, proteins present in nucleus were fractionated and extracted, western blot was performed using a specific antigen to a S-catenin protein (Santacruz, USA), and the expression change of a protein was confirmed.

As a result, as shown in FIG. 14, in the case of treating with the Trolox-peptide (SEQ ID NO: 2) conjugate, it was confirmed that the amount of the β-catenin present in the nucleus was markedly increased.

From the results above, it could be found that the promoting effects of hair growth were shown by activating the Wnt cell signal transduction by the Trolox-peptide (SEQ ID NO: 2) conjugate.

[7-3] Cell Signal Transduction Effects of Trolox-Peptide (SEQ ID NO: 3) Conjugate The HFDPC cells were treated with a Trolox-peptide (SEQ ID NO: 3) conjugate of 5 μM or 50 μM, and additionally cultivated for 15 minutes. Then, the cells were recovered, proteins present in nucleus were fractionated and extracted, and western blot was performed using a specific antigen to p-Erk 1/2 and p-Akt proteins (Cell signaling, USA) to confirm the expression change of the protein.

As a result, as shown in FIG. 15, in the case of treating with the Trolox-peptide (SEQ ID NO: 3) conjugate, it was confirmed that the phosphorylation of Erk 1/2 and Akt was significantly increased. Such increasing effects of phosphorylation was confirmed to increase further if the concentration of the Trolox-peptide conjugate for treatment was increased.

From the results above, it could be found that the promoting effects of hair growth were effectively induced by activating the KGF cell signal transduction involving the phosphorylation of Erk 1/2 and Akt by the Trolox-peptide (SEQ ID NO: 3) conjugate.

The present invention has been explained in detail by way of examples, but those skilled in the art will appreciate that various modifications and revisions may be made without departing from the scope of the technical concept, and such modifications and revisions are obviously included in the claims attached herein.

The invention claimed is:

1. A conjugate comprising 6-hydroxy-2,5,7,8-tetramethylchromane-2-carboxylic acid and a peptide, wherein the conjugate has a structure represented by Formula 1;

Formula 1

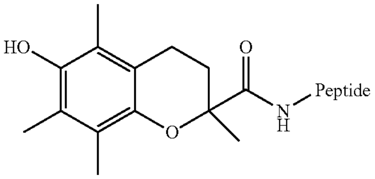

wherein the peptide has an amino acid sequence selected from the group consisting of SEQ ID NO: 1, SEQ ID NO: 2, and SEQ ID NO: 3.

2. The conjugate according to claim 1, wherein the peptide has the amino acid sequence of SEQ ID NO: 1 and the conjugate suppresses BMP 2 cell signal transduction.

3. The conjugate according to claim 1, wherein the peptide has the amino acid sequence of SEQ ID NO: 2 and the conjugate activates WNT cell signal transduction.

4. The conjugate according to claim 1, wherein the peptide has the amino acid sequence of SEQ ID NO: 3 and the conjugate activates KGF cell signal transduction.

5. A pharmaceutical composition for treating or reducing hair loss or promoting hair growth, comprising the conjugate of claim 1 as an effective ingredient.

6. A cosmetic composition for preventing treating or reducing hair loss or promoting hair growth, comprising the conjugate of claim 1 as an effective ingredient.

7. The cosmetic composition according to claim 6, wherein the cosmetic composition has any one formulation selected from the group consisting of emollient beauty washes, nutrition beauty washes, nutrition creams, massage creams, essences, eye creams, cleansing creams, cleansing foams, cleansing waters, packs, sprays, powders, hair tonics, hair creams, hair lotions, hair shampoos, hair rinses, hair conditioners, hair sprays, hair air-sols, pomades, sol-gels, emulsions, oils, waxes, or air-sols.

8. A method of treating or reducing hair loss in a subject in need thereof, the method comprising administering to the subject a composition comprising an effective amount of the conjugate of claim 1.

9. A method of promoting hair growth in a subject in need thereof, the method comprising administering to the subject a composition comprising an effective amount of the conjugate of claim 1.

* * * * *